(12) United States Patent
Hu et al.

(10) Patent No.: US 10,690,735 B2
(45) Date of Patent: Jun. 23, 2020

(54) WIRELESS DETECTION COIL SYSTEM

(71) Applicant: Aivitae LLC, Los Altos, CA (US)

(72) Inventors: Bob Sueh-chien Hu, Los Altos Hills, CA (US); Ada Shuk-Yan Poon, Redwood City, CA (US)

(73) Assignee: Aivitae LLC, Redwood City, CA (US)

( * ) Notice: Subject to any disclaimer, the term of this patent is extended or adjusted under 35 U.S.C. 154(b) by 381 days.

(21) Appl. No.: 15/498,060

(22) Filed: Apr. 26, 2017

(65) Prior Publication Data

US 2017/0307700 A1 Oct. 26, 2017

Related U.S. Application Data

(60) Provisional application No. 62/327,449, filed on Apr. 26, 2016.

(51) Int. Cl.
*A61B 5/055* (2006.01)
*A61B 5/00* (2006.01)
G01R 33/36 (2006.01)
(Continued)

(52) U.S. Cl.
CPC ...... *G01R 33/34084* (2013.01); *A61B 5/0013* (2013.01); *A61B 5/055* (2013.01);
(Continued)

(58) Field of Classification Search
CPC .......... G01R 33/34084; G01R 33/3692; G01R 33/3628; G01R 33/3621; G01R 33/3415;
(Continued)

(56) References Cited

U.S. PATENT DOCUMENTS

2006/0279284 A1* 12/2006 Vaughan ............ G01R 33/3692
324/318
2008/0204021 A1* 8/2008 Leussler ............ G01R 33/3415
324/318
(Continued)

FOREIGN PATENT DOCUMENTS

WO 2016/196675 A1 12/2016

OTHER PUBLICATIONS

International Search Report and Written Opinion of the International Searching Authority dated Aug. 9, 2018 in related International Application No. PCT/US2018/027737, 9 pages.
(Continued)

*Primary Examiner* — Angela M Hoffa
*Assistant Examiner* — Aminah Asghar
(74) *Attorney, Agent, or Firm* — Pillsbury, Winthrop Shaw Pittman LLP

(57) ABSTRACT

In certain embodiments, a coil circuitry component may be configured to detect RF signals from excited spins of at least a region of an organism, where the coil circuitry component comprises a RF detection coil and a detuning circuit for detuning the RF detection coil. A coil signal detection component may be configured to extract at least some of the RF signals detected by the coil circuitry component and to convert the extracted RF signals from analog signal to digital signals. An excitation estimation component may be configured to estimate the excitation pulses from an excitation source and to generate a control timing signal from the estimated excitation pulses to set a state of the detuning circuit. A wireless communication component may be configured to wirelessly transmit the converted RF signals, the estimated excitation pulses, and the control timing signal to an external computer system.

20 Claims, 9 Drawing Sheets

(51) Int. Cl.
  *A41D 1/00* (2018.01)
  *G01R 33/3415* (2006.01)
  *G01R 33/34* (2006.01)

(52) U.S. Cl.
  CPC ........ *A61B 5/6802* (2013.01); *G01R 33/3692* (2013.01); *A41D 1/005* (2013.01); *A61B 2560/0214* (2013.01); *G01R 33/3415* (2013.01); *G01R 33/3621* (2013.01); *G01R 33/3628* (2013.01)

(58) Field of Classification Search
  CPC ..... A61B 5/6802; A61B 5/0013; A61B 5/055; A61B 2560/0214; A41D 1/005
  See application file for complete search history.

(56) References Cited

U.S. PATENT DOCUMENTS

| | | |
|---|---|---|
| 2009/0224158 A1 | 9/2009 | Haselman et al. |
| 2010/0182009 A1* | 7/2010 | Crozier ............ G01R 33/34046 324/322 |
| 2012/0098542 A1* | 4/2012 | Van Helvoort .... G01R 33/3657 324/322 |
| 2014/0097844 A1* | 4/2014 | Tomiha ................. G01R 33/30 324/321 |
| 2014/0218034 A1 | 8/2014 | Ishii et al. |
| 2015/0112187 A1* | 4/2015 | Petropoulos ......... A61B 5/0555 600/422 |
| 2015/0177346 A1* | 6/2015 | Mazurewitz ..... G01R 33/34084 324/309 |
| 2016/0261031 A1 | 9/2016 | Dion et al. |
| 2016/0270725 A1 | 9/2016 | Gray et al. |
| 2017/0176551 A1* | 6/2017 | Deunsing ............. G01R 33/288 |

OTHER PUBLICATIONS

International Preliminary Report on Patentability issued in corresponding PCT/US2018/027737 dated Nov. 7, 2019 (8 pages).

* cited by examiner

WIRELESS DETECTION COIL SYSTEM

RELATED APPLICATIONS

This application claims the benefit of U.S. Provisional Patent Application Ser. No. 62/327,449, filed on Apr. 26, 2016, entitled, "Wireless Detection Coil Array for Magnetic Resonance Imaging," which is hereby incorporated by reference herein in its entirety.

FIELD OF THE INVENTION

The invention relates to systems for detection of signals from signal sources excited by signals from excitation source and transmission of such detected signals, including, for example, such system's wireless transmission of free induction decay (FID) signals from a magnetic resonance imaging (MRI) detection coil array to an external computer system, such system's wireless receipt of control signals from the external computer system, such system's synchronization of a detection coil array with radio-frequency (RF) excitation pulses, and such system's power harvesting from the excitation fields.

BACKGROUND OF THE INVENTION

In conventional magnetic resonance imaging (MRI) systems, an excitation source emits radio frequency (RF) pulses during an excitation phase to excite the spins of MR-relevant nuclei in a particular region of a body (e.g., human body, non-human animal body, etc.) so that the spins themselves become sources of an RF signal. During the reception phase, the RF signals from the spins (e.g., free induction decay (FID) signals) may be measured, and the measurements may be used to generate one or more images with respect to the particular body region. Because the RF pulses (during the excitation phase) are of relatively high field strength, mechanisms are applied to detune the receiver coil during the excitation phase to protect the circuitry used in the reception phase. Such mechanisms may, for example, include pin diodes or switches, such as high-power FET (field-effect transistor) devices, HEMT (high-electron-mobility transistor) devices, etc., where control signals are used to toggle the states of these devices in real-time. In a typical MRI system, these control signals are routed to the receiver coil via cables from the excitation coil or a signal processing unit housed outside the magnet (or other excitation source), and the excitation and reception coils are connected to the signal processing unit via coaxial cables. To achieve better image quality or shorten the acquisition time, it is desirable to increase the number of receiver coils, but the increase typically results in increased cabling, which typically results in significant system complexity and costs for a conventional MRI system. These and other drawbacks exist.

SUMMARY OF THE INVENTION

Aspects of the invention relate to methods, apparatuses, and/or systems for facilitating detection of signals from signal sources excited by signals from excitation source and wireless transmission of such detected signals.

In certain embodiments, a coil circuitry component may be configured to detect RF signals from excited spins of at least a region of an organism, where the coil circuitry component comprises a RF detection coil and a detuning circuit for detuning the RF detection coil, and the spins of the region of the organism are excited by excitation pulses from an excitation source. A coil signal detection component may be configured to extract at least some of the RF signals detected by the coil circuitry component and to convert the extracted RF signals from analog signal to digital signals. An excitation estimation component may be configured to estimate the excitation pulses from the excitation source and to generate a control timing signal from the estimated excitation pulses to set a state of the detuning circuit. A wireless communication component may be configured to wirelessly transmit the converted RF signals, the estimated excitation pulses, and the control timing signal to a computer system external to the wireless detection coil system.

Various other aspects, features, and advantages of the invention will be apparent through the detailed description of the invention and the drawings attached hereto. It is also to be understood that both the foregoing general description and the following detailed description are exemplary and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise.

DETAILED DESCRIPTION OF THE INVENTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other instances, well-known structures and devices are shown in block diagram form in order to avoid unnecessarily obscuring the embodiments of the invention.

Figure 1A:
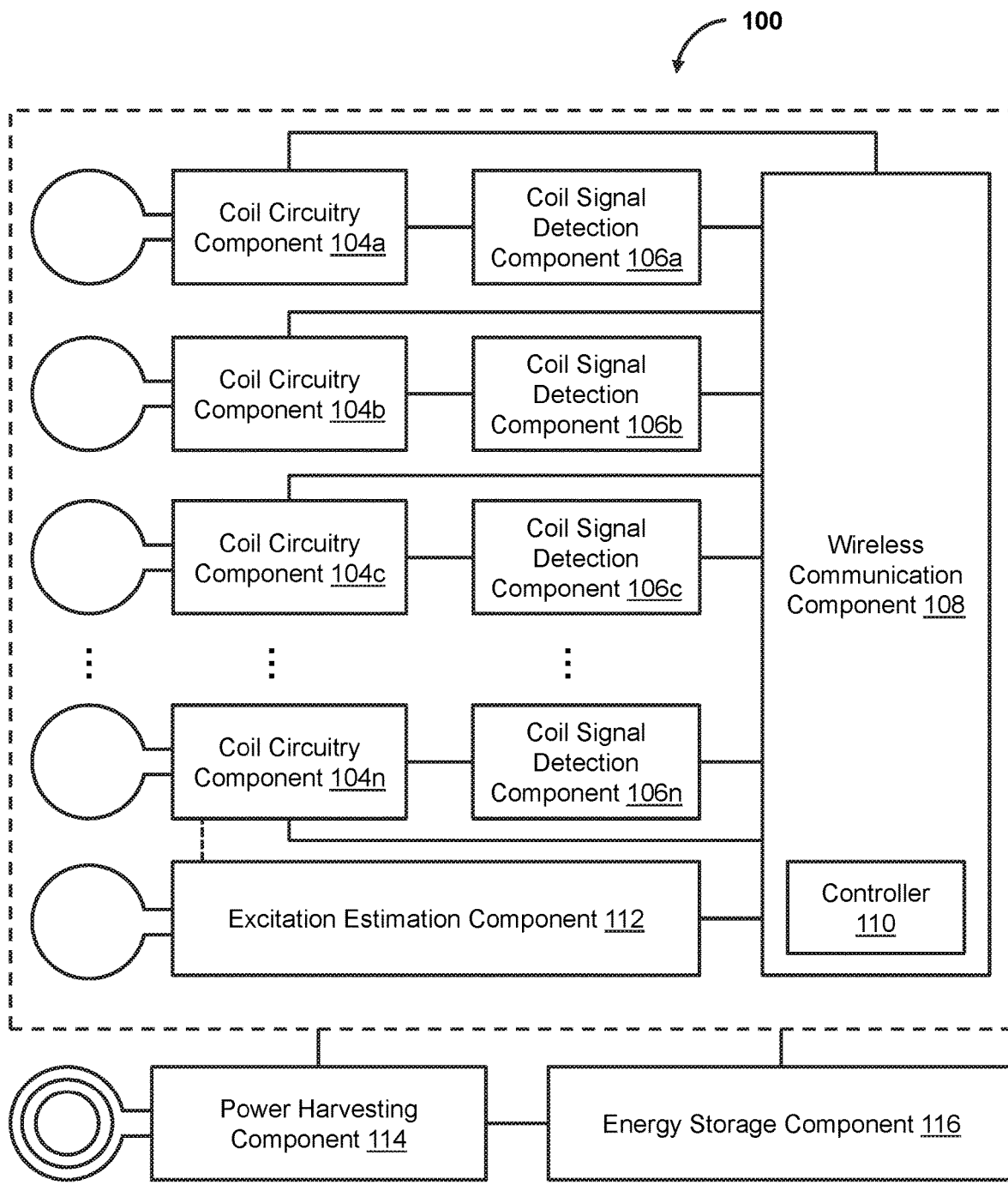
FIG. 1A shows a diagram of a wireless detection coil system, in accordance with one or more embodiments.

In some embodiments, a system may include one or more servers, client devices, or other components that interact with one or more wireless detection coil systems. As an example, one or more servers or client devices may interact with a wireless detection coil system to provide commands or other information as input to the wireless detection coil system, to obtain information as output for presentation to one or more users, or perform other actions with respect to the wireless detection coil system. In some embodiments, with respect to FIG. 1A, a wireless detection coil system 100 may include one or more of coil circuitry components 104 (e.g., coil circuitry components 104a-104n), coil signal detection components 106 (e.g., coil signal detection components 106a-106n), a wireless communication component 108, a controller 110, an excitation estimation component 112, a power harvesting component 114, an energy storage component 116, or other components. As an example, with respect to the reception phase, one or more coil circuitry components 104 may pick up FID signals from excited spins in a particular region of a body (e.g., human body, non-human animal body, etc.), and the corresponding coil signal detection components 106 may detect and extract the FID signals from the coils (e.g., with the highest possible signal-to-noise ratio (SNR)). The wireless communication component 108 may wirelessly transmit the detected FID signals to a signal processing unit (e.g., a computer system external to the wireless detection coil system 100 or other external signal processing unit).

Figure 1B:
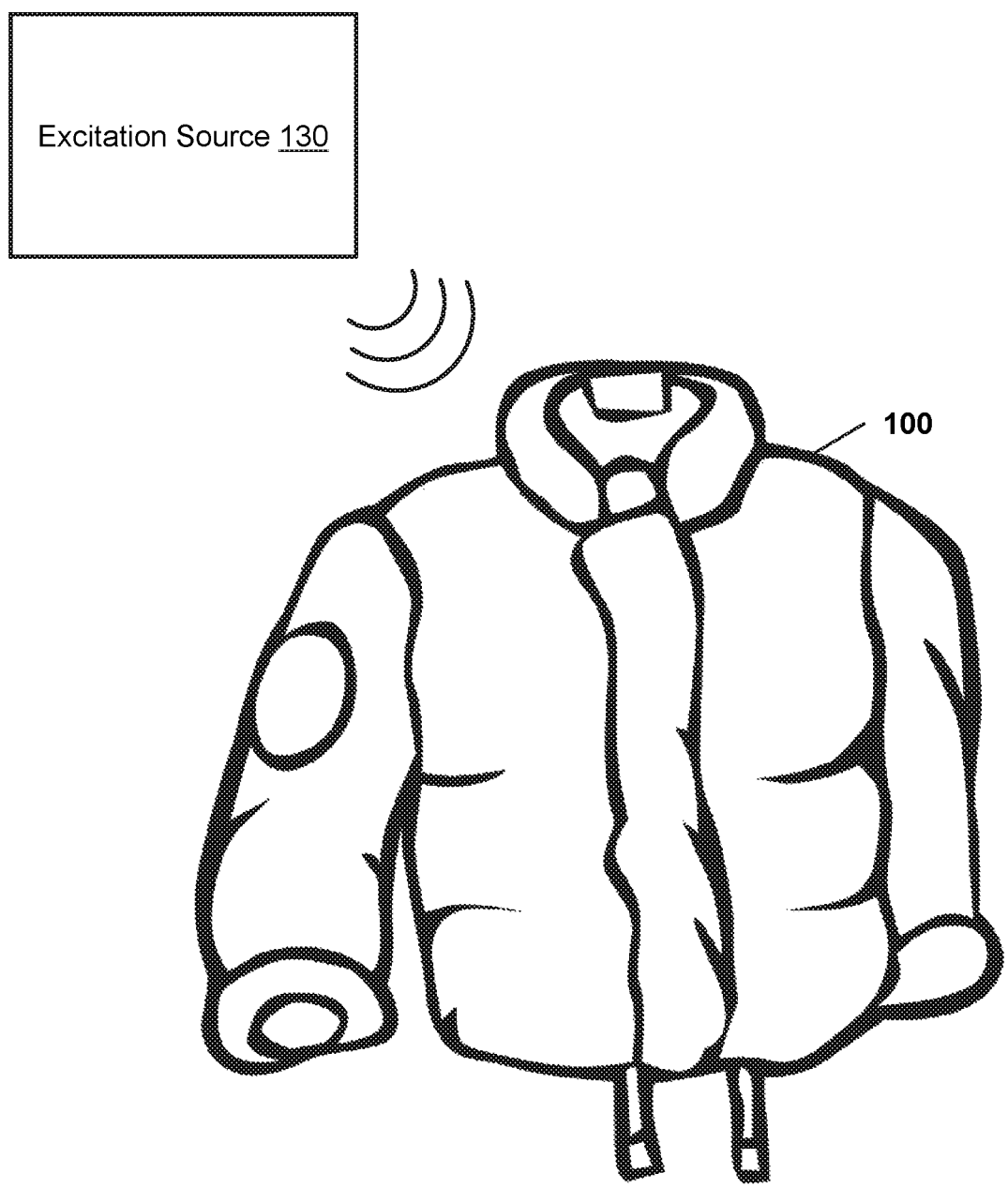
FIG. 1B shows a diagram of a wearable wireless detection coil system and an excitation source to excite the spins of MR-relevant nuclei in a wearer of the wearable wireless detection coil system, in accordance with one or more embodiments.

As another example, with respect to the excitation phase, one or more techniques may be performed to protect the circuitry used in the reception phase. In one use case, the excitation estimation component 112 (e.g., an excitation pulse estimator) may measure RF excitation pulses from an excitation source (e.g., excitation source 130 shown in FIG. 1B) and generate control signals for the coil circuitry components 104 (e.g., to activate detuning circuits in the coil circuitry components 104 to turn the coils therein when the RF excitation pulse is present or any other condition that may damage the coil signal detection components 106 is present). In some cases, the wireless communication component 108 (e.g., via controller 110) may pass the generated control signals to the coil circuitry components 104. In some cases, excitation estimation component 112 may send the generated control signals to the coil circuitry components 104 (e.g., via a direct connection thereto or via other means) without the generated control signals being passed from the wireless communication component 108 to the coil circuitry components 104. In this way, for example, the wireless detection coil system may eliminate or reduce the need for cables that connect the coil circuitries to external signal processing units (which provide the control signals via the cables to toggle the states of these devices to protect the coil circuitries), thereby reducing system complexities and costs associated with conventional MRI or other systems (e.g., even when increasing the number of coils to achieve better image quality or shorten the acquisition time).

In some embodiments, with respect to FIG. 2, the wireless detection coil system 100 may be implemented in the form of a wearable device, such as a jacket, a shirt, pants, shoes, headgear (e.g., helmet, hat, etc.), socks, sleeves, a wearable band, or other wearable device (e.g., due to significant reductions in complexity or size of the wireless detection coil system 100, as compared to conventional MIII or other systems, as a result of the lack of cables that were typically used for sending control signals from external signal processing units to the coil circuitries). In some embodiments (e.g., where the wireless detection coil system 100 has coil circuitry components 104 not associated with regions of the body that are to be imaged), an external computer system (or other signal processing unit) may wirelessly transmit instructions to controller 110 (e.g., via a wireless transceiver or receiver of the wireless communication component 108), and controller 110 may send the control signals to those coil circuitry components 104 to activate the detuning circuits therein (e.g., to turn off the coils therein).

In some embodiments, one or more of the coil circuitry components 104 or coil signal detection components 106 may be at least part of respective modular units (e.g., in the form of wearable sleeves, wearable bands, other wearables, or other forms) configured to be pluggable into the wireless detection coil system 100 to add more coil subsystems to the wireless detection coil system 100 in a "plug and play" manner (e.g., by directly connecting additional coil subsystems to coil subsystems already connected to the wireless detection coil system 100 or to other components of the wireless detection coil system 100). As an example, (i) a first coil subsystem may include the coil circuitry component 104a and the coil signal detection component 106a; (ii) a second coil subsystem may include the coil circuitry component 104b and the coil signal detection component 106b; (iii) a third coil subsystem may include the coil circuitry component 104c and the coil signal detection component 106c; and (iv) so on. As another example, the coil subsystems may each include one or more coil circuitry components 104 and one or more coil signal detection components 106. Each of the coil subsystems (or their individual components 104 or 106) may be configured to be pluggable into the wireless detection coil system 100 in a plug and play manner.

In some embodiments, the power harvesting component 114 may convert energy from the excitation field (e.g., emitted by an excitation source during the excitation phase) to charge the energy storage component 116 (e.g., one or more rechargeable batteries, one or more high density capacitors, etc.). In one use case, one or more components of the wireless detection coil system 100 may be partially or fully powered by the energy storage component 116 (e.g., coil circuitry component 104, coil signal detection component 106, wireless communication component 108, controller 110, excitation estimation component 112, power harvesting component 114, etc.) may be powered through the energy storage component 116).

Figure 2A:
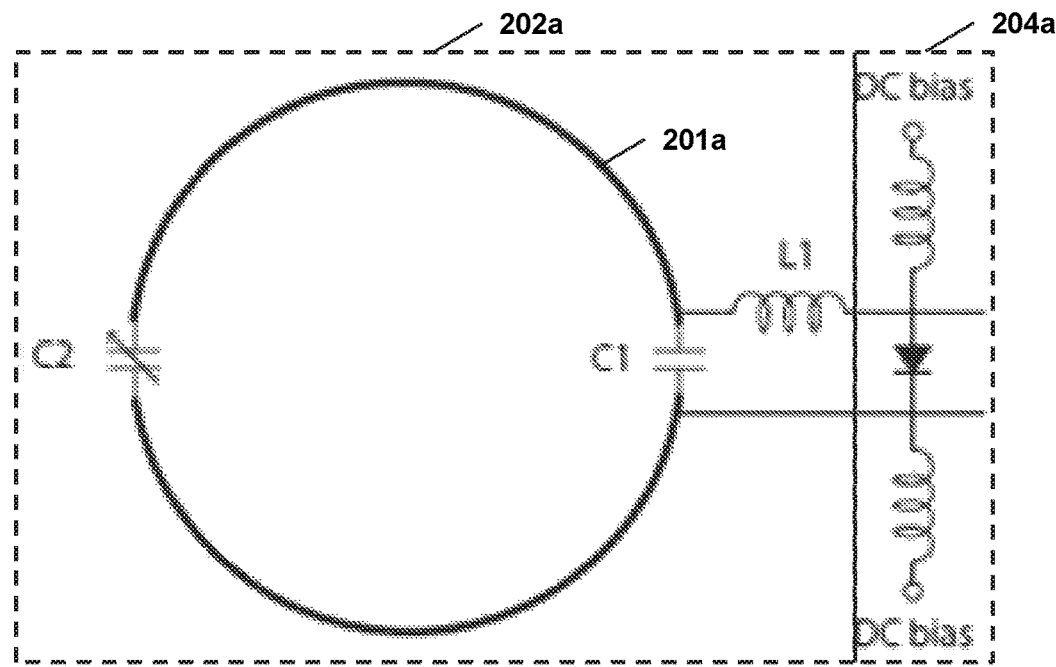
FIG. 2A shows a diagram of a coil circuitry component, in accordance with one or more embodiments.
Figure 2B:
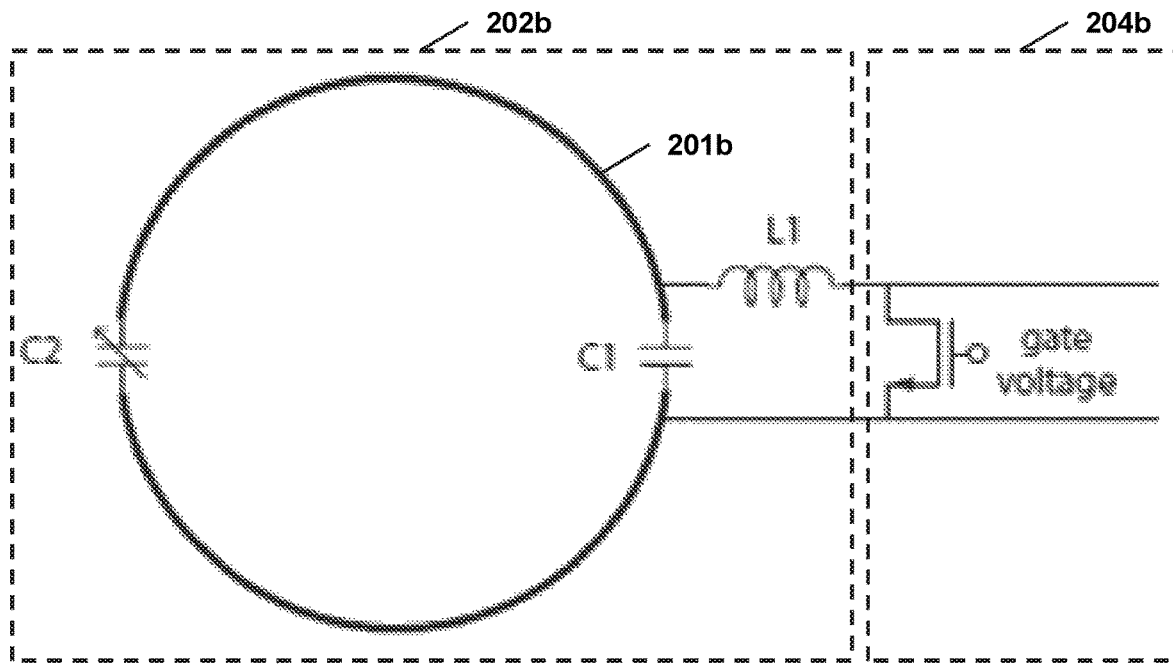
FIG. 2B shows another diagram of a coil circuitry component, in accordance with one or more embodiments.

In some embodiments, with respect to FIGS. 2A and 2B, the coil circuitry component 104 may include a coil 201, a tuning and matching circuit 202 (e.g., circuit 202a, circuit 202b, etc.), a detuning circuit 204 (e.g., circuit 204a, circuit 204b, etc.), or other components. As an example, the tuning and matching circuit 202 (e.g., including C1, C2, and L1) may tune the coil to resonant at the Larmor frequency and transforms the coil impedance to the desired noise matching impedance of a preamplifier in the coil signal detection component 106 (e.g., a preamplifier in a FID detection circuit thereof). As shown in FIG. 2A, the coil circuitry component 104 may include the detuning circuit 204a, which includes a pin diode and requires DC bias current to activate it. As an example, the bias current that is required for activation may be in the range of 10 ma to 100 mA (or other bias current ranges). As shown in FIG. 2B, in some cases, a lower power implementation of a detuning circuit in the form of the detuning circuit 204b may be utilized as part of the coil circuitry component 104. The detuning circuit 204 may include a high-power RF switch, such as a FET device, a HEMT device, etc. A control signal may be applied to the gate of the transistor (e.g., FET, HEMT, etc.) to turn the transistor on or off.

Figure 2C:
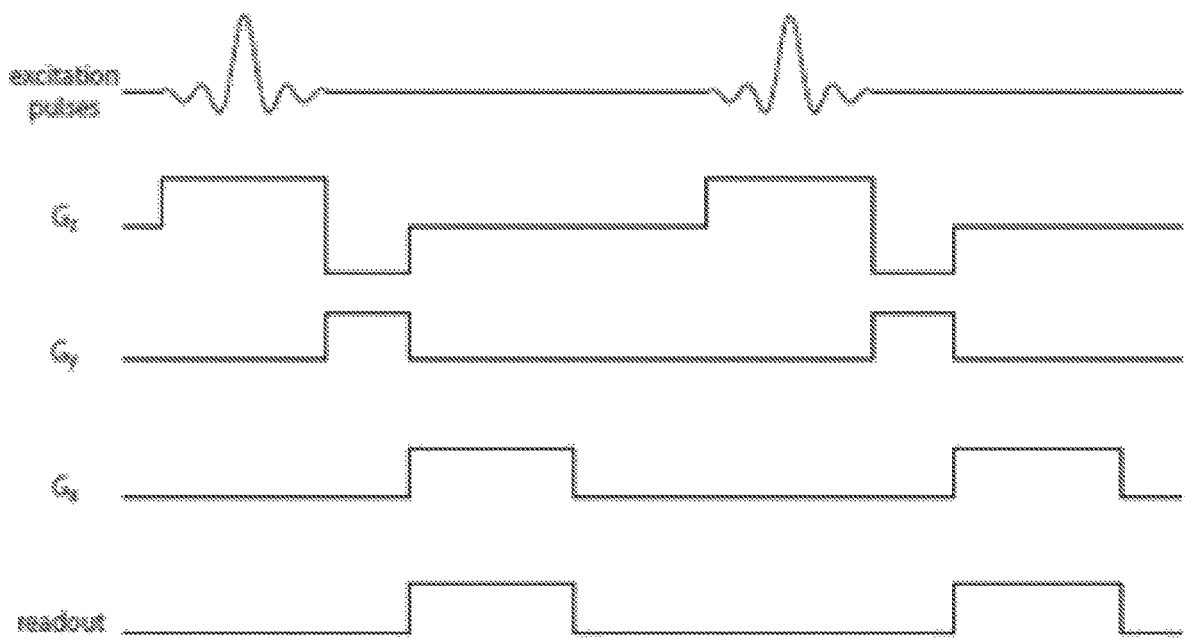
FIG. 2C shows a timing diagram of an excitation and detection sequence, in accordance with one or more embodiments.

As an example, FIG. 2C shows a timing diagram of an excitation and reception sequence for a 2D Fourier transform image projection-reconstruction method. In one use case, with respect to FIG. 2C, gradient fields, Gz, Gy, and Gx are applied to select a specific region of the body to be imaged. An RF excitation pulse is applied to excite that specific region. In conventional MRI systems, the signal readout generally occurs in the presence of the Gx gradient field. The pin diode in FIG. 2A and the RF switch in FIG. 2B are turned on when the RF excitation pulses are applied. They are turned off during the signal readout periods. The ON/OFF control signal is typically provided by the external processing unit via a cable. As discussed, in some embodiments of the invention, the ON/OFF control signal is generated within the wireless detection coil system 100. For example, the generation of the ON/OFF control signal may be performed by the excitation estimation component 112 of the wireless detection coil system 100. In one use case, with respect to FIG. 3A, the excitation estimation component 112 may include a coil 302 (e.g., to pick up the excitation field), an attenuator 304, an envelope detector 306, an analog-to-digital converter (ADC) 308, and a control-signal generator 310. Because the excitation pulses are of relatively high field strength, the attenuator 304 may be used to scale the magnitude of the induced signal to fall within the input range of the envelop detector 306. The envelop detector 306 yields an estimate of the excitation pulses. From the estimates, the control-signal generator 310 may generate a control signal to activate the detuning circuits in the coil circuitry components 104 (e.g., detuning circuits 204a, detuning circuits 204b, etc., of the coil circuitry components 104). As indicated in the timing diagram of FIG. 3B, the control-signal generator may be a threshold detector in some embodiments. Other forms of the control-signal generator may be utilized in other embodiments.

Figure 3A:
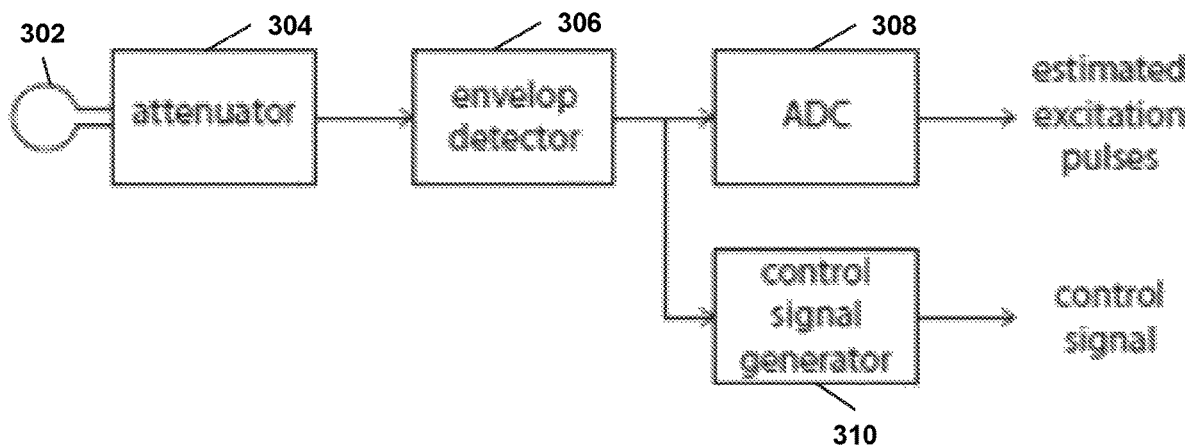
FIG. 3A shows a diagram of an excitation estimation component, in accordance with one or more embodiments.
Figure 3B:
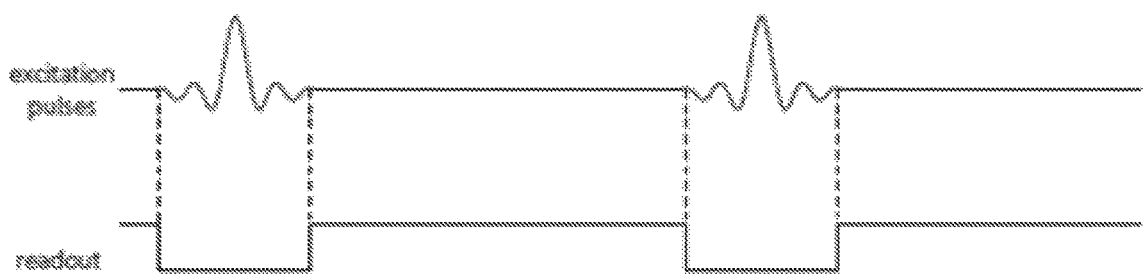
FIG. 3B shows a diagram of a timing diagram of excitation and FID detection, in accordance with one or more embodiments.

In a further use case, with respect to FIG. 3A, the digitized estimated excitation pulses (e.g., as an output of ADC 308) and the ON/OFF control signal (e.g., control timing signal that activates the detuning circuits of the coil circuitry components 104 to turn off the coils thereof) may be wirelessly transmitted to an external computer system (or other external processing unit) via the wireless communication component 108. Given that the external computer system knows the timing of the excitation pulses and the gradient fields, the external computer system may extract the portion of readout data for image reconstruction upon receiving the wirelessly-transmitted information (e.g., generated one or more sub-components of the excitation estimation component 112).

Figure 4:
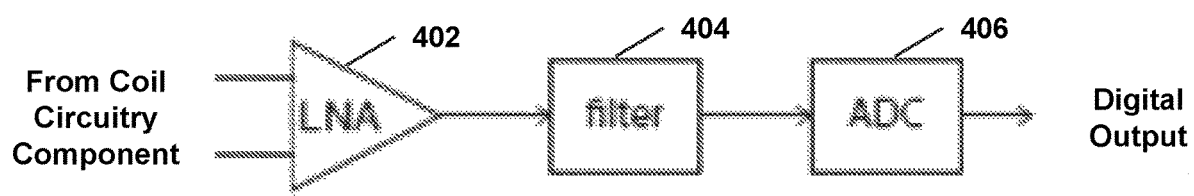
FIG. 4 shows a diagram of a coil signal detection component, in accordance with one or more embodiments.

In some embodiments, with respect to FIG. 4, the coil signal detection component 106 may include a low-noise preamplifier (LNA) 402, a filter 404 (e.g., a low-pass or bandpass filter), and a high-speed analog-to-digital converter (ADC) 406. As an example, FID signals received from the coil circuitry component may be amplified by the LNA 104 and then filtered by the filter 406 (e.g., low-pass or bandpass filtering). The signals (e.g., that are outputted by the filter 406) may then be directly digitized by the high-speed ADC 406. As another example, the coil signal detection component 106 may include one or more decimation filters, which may be used to decimate the digital signals (from the high-speed ADC 406). The decimated digital signals may be provided as output to the wireless communication component 108.

Figure 5:
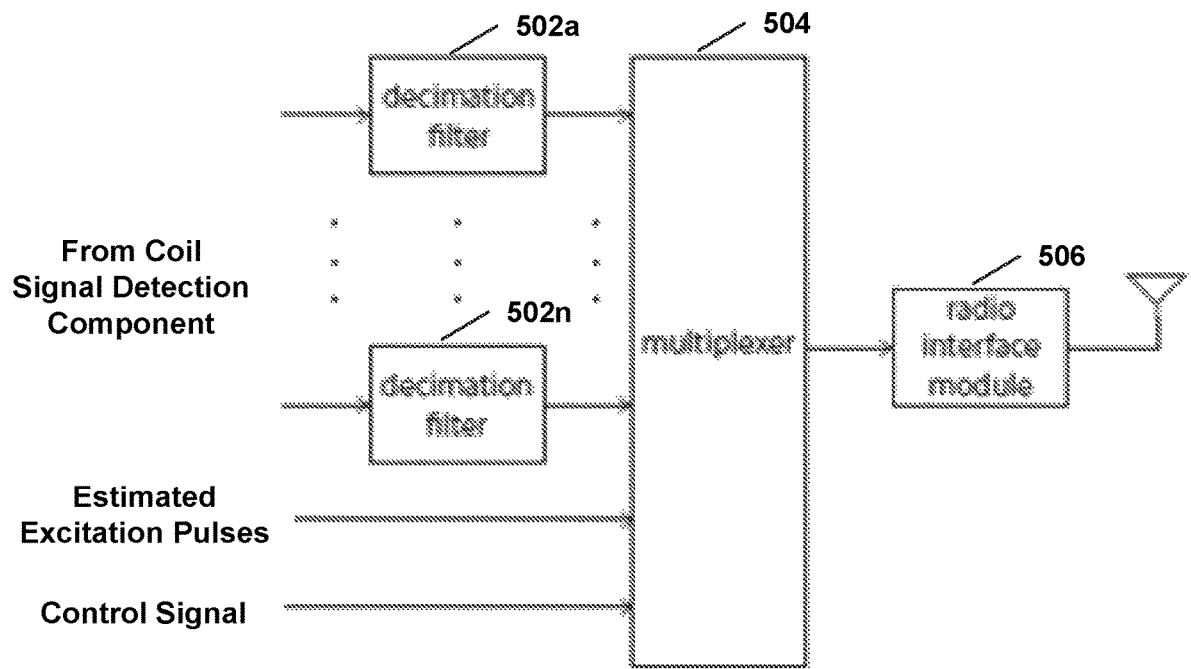
FIG. 5 shows a diagram of a wireless communication component, in accordance with one or more embodiments.

In some embodiments, with respect to FIG. 5, the wireless communication component 108 may include an array of decimation filters 502, a multiplexer 504, a radio interface module 506, or other components (e.g., controller 110, antenna, etc.). As an example, digital outputs from the coil signal detection components 106 (e.g., FID detection circuits of the coil signal detection components 106) may first be decimated via the decimation filters 504a to reduce the data-rate requirement on the radio interface module 506. In addition, the decimated outputs, the estimated excitation pulses (e.g., from the excitation estimation component 112), and the ON/OFF control signal (e.g., from the excitation estimation component 112) may be multiplexed and directed to the radio interface module 506. The radio interface module 506 may wirelessly transmit the multiplexed data to an external computer system (or other signal processing unit). The external computer system may then generate one or more images based on the transmitted multiplexed data. In some embodiments, the air interface module 506 may utilize the IEEE 802.11ac standard. In some embodiments, the air interface module 506 may utilize the IEEE 802.11ad standard.

Figure 6:
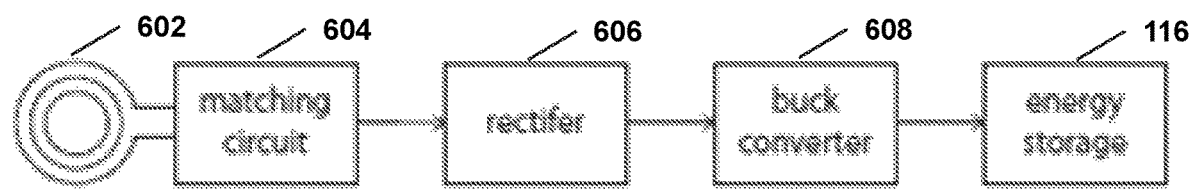
FIG. 6 shows a diagram of a power harvesting component, in accordance with one or more embodiments.

In some embodiments, the power harvesting component 114 may convert energy from the excitation field (e.g., emitted by an excitation source during the excitation phase) to charge the energy storage component 116 (e.g., one or more rechargeable batteries, one or more high density capacitors, etc.). One or more components of the wireless detection coil system 100 may be partially or fully powered by the energy storage component 116 may be powered through the energy storage component 116). As an example, for a 1.5-Tesla Mill system and a typical excitation field strength of 10 µT and 10% duty cycle, a coil having a 3-inch diameter may be used to harvest about 4 W of power (e.g., per [please insert here]). As such, cascading a few of these coils, increasing the number of turns, etc., may enable harvesting of 10's of watts of power. In some embodiments, with respect to FIG. 6, the power harvesting component 114 may include a one-turn or multi-turn coil 602, a matching circuit 604, a rectifier 606, a buck converter 608, and the energy storage component 116. In one use case, the matching circuit 604 may transform the coil impedance of coil 602 to match with the load impedance of rectifier 606. The rectifier 606 may convert the AC (alternating current) signal (from the matching circuit 604) into a DC (direct current) signal. The buck converter 608 may perform DC-DC conversion (of the DC signal from the rectifier 606) and produce a lower-voltage DC signal that matches with the input voltage of the energy storage component 116.

Figure 7:
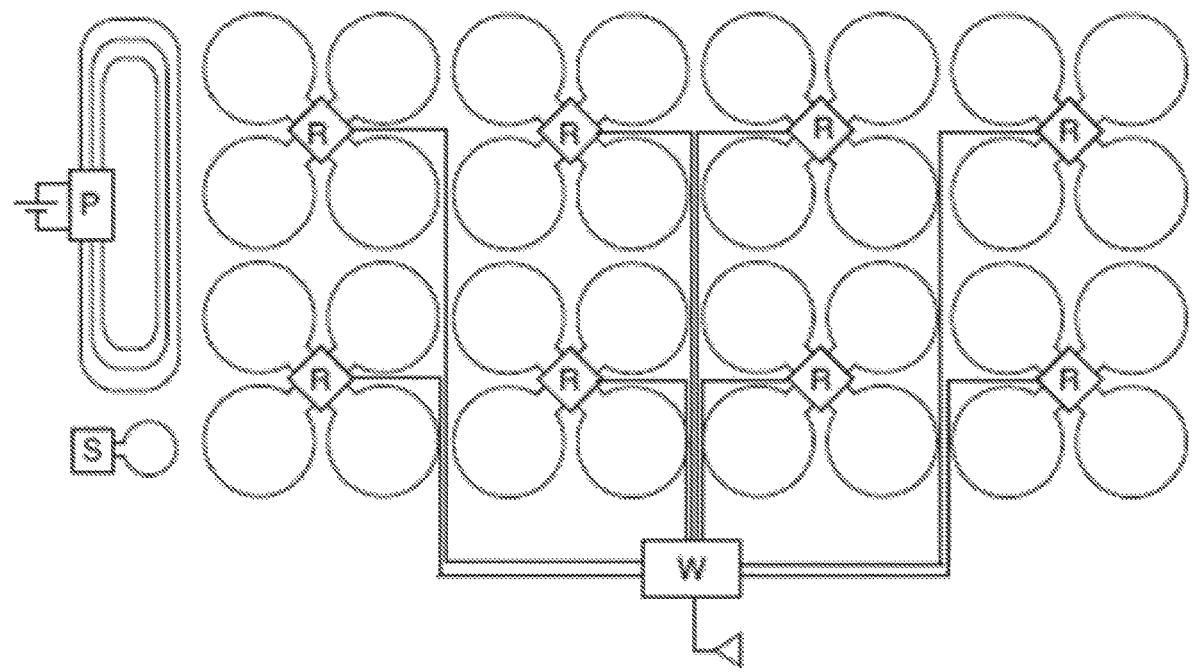
FIG. 7 shows a diagram of a modular detection coil system, in accordance with one or more embodiments.

In some embodiments, one or more of the coil circuitry components 104 or coil signal detection components 106 may be at least part of respective modular units. In some embodiments, with respect to FIG. 7, the components 104 and 106 may be arranged together as a set of 8 (or other number) of sub-arrays to form a coil array for the wireless detection coil system 100. As shown in FIG. 7, for example, each sub-array (of a 8-sub-array coil array) may include 4 coils, the corresponding detuning circuit, and a FID detection circuit. Digital lines may be routed from each sub-array to the wireless communication component 108 (e.g., a wireless transmitter). As another example, the excitation estimation component 112 (e.g., a excitation pulse estimator) may measures the RF excitation pulses and creates control signals for the detuning circuit in each sub-array. As a further example, the power harvesting component 114 (e.g., a power harvester) may convert energy from the excitation field to charge the energy storage component 116.

As such, for instance, energy for the operation of each sub-array, the excitation pulse estimator, and the wireless transmitter may be obtained from this storage element (e.g., the energy storage component 116 may partially or fully power such components).

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

1. A wireless detection coil system comprising: a coil circuitry component configured to detect RF signals from excited spins of at least a region of an organism, the coil circuitry component comprising a RF detection coil and a detuning circuit for detuning the RF detection coil, the spins of the region of the organism being excited by excitation pulses from an excitation source; a coil signal detection component configured to extract at least some of the RF signals detected by the coil circuitry component and to convert the extracted RF signals from analog signal to digital signals; and an excitation estimation component configured to: estimate the excitation pulses from the excitation source; generate a control timing signal from the estimated excitation pulses to set a state of the detuning circuit; and a wireless communication component configured to wirelessly transmit the converted RF signals, the estimated excitation pulses, and the control timing signal to a computer system external to the wireless detection coil system, the external computer system being configured to generate one or more images based on the converted RF signals, the estimated excitation pulses, and the control timing signal.
2. The wireless detection coil system of embodiment 1, wherein the wireless detection coil system is integrated as at least part of a wearable device such that the wearable device comprises the coil circuitry component, the coil signal detection component, the excitation estimation component, and the wireless communication component.
3. The wireless detection coil system of embodiment 2, wherein the external computer system is external to the wearable device.
4. The wireless detection coil system of embodiments 1 or 2, further comprising: a plurality of modular units comprising a first modular unit and a second modular unit, wherein each of the first modular unit and the second modular unit comprises at least one coil circuitry component and at least one coil signal detection component, the first module unit comprising the coil circuitry component and the coil signal detection component, and wherein the first modular unit is directly connected to the second modular unit.
5. The wireless detection coil system of any of embodiments 1-3, further comprising: a power harvesting component configured to convert energy from an excitation field emitted by the excitation source into DC current signals; and an energy storage component configured to store the converted energy and to power one or more components of the wireless detection coil system.

6. A method comprising: detecting, by a RF detection coil, RF signals from excited spins of at least a region of an organism, the spins of the region of the organism being excited by excitation pulses from an excitation source; extracting, by a FID detection circuit, at least some of the detected RF signals; converting, by the FID detection circuit, the extracted RF signals from analog signal to digital signals; estimating, by an excitation estimator, the excitation pulses from the excitation source; generating, by the excitation estimator, a control timing signal from the estimated excitation pulses to set a state of a detuning circuit for detuning the RF detection coil; and wirelessly transmitting, via a wireless transmitter, the converted RF signals, the estimated excitation pulses, and the control timing signal to a computer system.
7. The method of embodiment 6, wherein the detecting operation, the extracting operation, the estimating operation, the generating operation, and the wireless transmitting operation is performed by a wearable device that comprises the RF detection coil, the FID detection circuit, the excitation estimator, and the wireless transmitter.
8. The method of embodiment 7, wherein the computer system is external to the wearable device.
9. The method of any of embodiments 6-8, wherein the coil circuitry component and the coil signal detection component are at least part of a first modular unit, the method further comprising: detecting, by a controller, a second modular unit being physically connected to the first modular unit, the second modular unit comprise at least one coil circuitry component and at least one coil signal detection component; obtaining, by the controller, modular-unit information from the second modular unit based on the detection of the second modular unit; and wirelessly transmitting, via the wireless transmitter, status information to the external computer system based on the modular-unit information.
10. The method of embodiment 9, wherein the modular-unit information comprises manufacturing information indicating one or more manufacturers of one or more components of the second modular unit, model information indicating one or more models of one or more components of the second modular unit, information indicating a number of components in the second modular unit, or information indicating one or more types of components in the second modular unit.
11. The method of embodiments 9 or 10, wherein the status information comprises the modular-unit information, overall-modular-units information indicating the number or types of modular units connected as at least part of a wireless detection coil system.
12. The method of any of embodiments 6-11, further comprising: converting, by a power harvesting component, energy from an excitation field emitted by the excitation source into DC current signals; storing, an energy storage component, the converted energy; and powering, by the energy storage component, the FID detection circuit, the excitation estimator, or the wireless transmitter.

What is claimed is:
1. A wireless detection coil system comprising:
a coil circuitry component configured to detect RF signals from excited spins of at least a region of an organism, the coil circuitry component comprising a RF detection coil and a detuning circuit for detuning the RF detection coil, the spins of the region of the organism being excited by excitation pulses from a source;
a coil signal detection component configured to extract at least some of the RF signals detected by the coil circuitry component and to convert the extracted RF signals from analog signal to digital signals; and an excitation estimation component (i) comprising an attenuator and an envelope detector and (ii) configured to:

estimate, via the attenuator and the envelope detector, one or more values corresponding to the excitation pulses from the source;

generate a control timing signal from the one or more estimated values corresponding to the excitation pulses to set a state of the detuning circuit; and a wireless communication component configured to wirelessly transmit the one or more estimated values corresponding to the excitation pulses along with the converted RF signals, and the control timing signal to a computer system external to the wireless detection coil system, the external computer system being configured to generate one or more images based on the converted RF signals, the one or more estimated values corresponding to the excitation pulses, and the control timing signal.

2. The wireless detection coil system of claim 1, wherein the wireless detection coil system is integrated as at least part of a wearable device such that the wearable device comprises the coil circuitry component, the coil signal detection component, the excitation estimation component, and the wireless communication component.

3. The wireless detection coil system of claim 2, wherein the external computer system is external to the wearable device.

4. The wireless detection coil system of claim 1, further comprising:

a plurality of modular units comprising a first modular unit and a second modular unit, wherein each of the first modular unit and the second modular unit comprises at least one coil circuitry component and at least one coil signal detection component, the first modular unit comprising the coil circuitry component and the coil signal detection component, and wherein the first modular unit is directly connected to the second modular unit.

5. The wireless detection coil system of claim 1, further comprising:

a power harvesting component configured to convert energy from an excitation field emitted by the source into DC current signals; and an energy storage component configured to store the converted energy and to power one or more components of the wireless detection coil system.

6. A method comprising:

detecting, by a RF detection coil, RF signals from excited spins of at least a region of an organism, the spins of the region of the organism being excited by one or more excitation pulses from a source;

extracting, by a FID detection circuit, at least some of the detected RF signals;

converting, by the FID detection circuit, the extracted RF signals from analog signal to digital signals;

estimating, by an attenuator and an envelope detector of an excitation pulse estimator, one or more values corresponding to the excitation pulses from the source;

generating, by the excitation pulse estimator, a control timing signal based on the one or more estimated values corresponding to the excitation pulses to set a state of a detuning circuit for detuning the RF detection coil; and wirelessly transmitting, via a wireless transmitter, the one or more estimated values corresponding to the excitation pulses along with the converted RF signals, and the control timing signal to a computer system.

7. The method of claim 6, wherein the detecting operation, the extracting operation, the converting operation, the estimating operation, the generating operation, and the wireless transmitting operation is performed by a wearable device that comprises the RF detection coil, the FID detection circuit, the excitation pulse estimator, and the wireless transmitter.

8. The method of claim 7, wherein the computer system is external to the wearable device.

9. The method of claim 6, wherein the RF detection coil and the FID detection circuit are at least part of a first modular unit, the method further comprising:

detecting, by a controller, a second modular unit being physically connected to the first modular unit, the second modular unit comprise at least one RF detection coil and at least one FID detection circuit;

obtaining, by the controller, modular-unit information from the second modular unit based on the detection of the second modular unit; and wirelessly transmitting, via the wireless transmitter, status information to the computer system based on the modular-unit information.

10. The method of claim 9, wherein the modular-unit information comprises manufacturing information indicating one or more manufacturers of one or more components of the second modular unit, model information indicating one or more models of one or more components of the second modular unit, information indicating a number of components in the second modular unit, or information indicating one or more types of components in the second modular unit.

11. The method of claim 9, wherein the status information comprises the modular-unit information, the modular-unit information indicating the number or types of modular units connected as at least part of a wireless detection coil system.

12. The method of claim 6, further comprising:

converting, by a power harvesting component, energy from an excitation field emitted by the source into DC current signals;

storing, an energy storage component, the converted energy; and powering, by the energy storage component, the FID detection circuit, the excitation pulse estimator, or the wireless transmitter.

13. The method of claim 6, wherein the source comprises an excitation source configured to emit RF pulses.

14. The wireless detection coil system of claim 1, wherein the source comprises an excitation source configured to emit RF pulses.

15. A wireless detection coil system comprising:

a first circuit to detect RF signals from excited spins of at least a region of an organism, the first circuit comprising a RF detection coil and a detuning circuit for detuning the RF detection coil, the spins of the region of the organism being excited by excitation pulses from a source;

a second circuit to extract at least some of the RF signals detected by the first circuit and to convert the extracted RF signals from analog signal to digital signals; and a third circuit, comprising an attenuator and an envelope detector, to:

estimate, via the attenuator and the envelope detector, one or more values corresponding to the excitation pulses from the source;

generate a control timing signal from the one or more estimated values corresponding to the excitation pulses to set a state of the detuning circuit; and a fourth circuit to wirelessly transmit the one or more estimated values corresponding to the excitation pulses along with the converted RF signals, and the control timing signal to a computer system external to the wireless detection coil system, the external computer system being configured to generate one or more images based on the converted RF signals, the one or more estimated values corresponding to the excitation pulses, and the control timing signal.

16. The wireless detection coil system of claim 15, wherein the wireless detection coil system is integrated as at least part of a wearable device such that the wearable device comprises the first circuit, the second circuit, the third circuit, and the fourth circuit.

17. The wireless detection coil system of claim 16, wherein the external computer system is external to the wearable device.

18. The wireless detection coil system of claim 15, further comprising:

a plurality of modular units comprising a first modular unit and a second modular unit, wherein each of the first modular unit and the second modular unit comprises at least one first circuit and at least one second circuit, the first modular unit comprising the first circuit and the second circuit, and wherein the first modular unit is directly connected to the second modular unit.

19. The wireless detection coil system of claim 15, further comprising:

a power harvesting component configured to convert energy from an excitation field emitted by the source into DC current signals; and a battery to store the converted energy and to power one or more components of the wireless detection coil system.

20. The wireless detection coil system of claim 15, wherein the source comprises an excitation source configured to emit RF pulses.

* * * * *